US008847120B2

(12) United States Patent
Burkett et al.

(10) Patent No.: US 8,847,120 B2
(45) Date of Patent: Sep. 30, 2014

(54) SYSTEMS AND METHODS OF IMPLEMENTING AN ELECTRODE FOR COOKING MEDIUM QUALITY MEASUREMENT

(75) Inventors: Douglas A. Burkett, Eaton, OH (US); Edmond L. Phillipps, Jr., Cincinnati, OH (US)

(73) Assignee: Henny Penny Corporation, Eaton, OH (US)

( * ) Notice: Subject to any disclaimer, the term of this patent is extended or adjusted under 35 U.S.C. 154(b) by 415 days.

(21) Appl. No.: 13/215,158

(22) Filed: Aug. 22, 2011

(65) Prior Publication Data
US 2012/0074125 A1 Mar. 29, 2012

Related U.S. Application Data

(60) Provisional application No. 61/375,851, filed on Aug. 22, 2010.

(51) Int. Cl.
*G01N 27/06* (2006.01)
*G01N 27/22* (2006.01)
*A47J 37/12* (2006.01)
*G01N 27/07* (2006.01)
*G01N 33/03* (2006.01)

(52) U.S. Cl.
CPC ............... *G01N 27/07* (2013.01); *G01N 33/03* (2013.01); *A47J 37/1266* (2013.01)
USPC ............. 219/439; 99/403; 324/448; 324/449; 324/698

(58) Field of Classification Search
None
See application file for complete search history.

(56) References Cited

U.S. PATENT DOCUMENTS

| 3,047,797 A | | 7/1962 | Borsboom | |
|---|---|---|---|---|
| 3,432,750 A | * | 3/1969 | Botstiber | 324/439 |
| 3,746,974 A | * | 7/1973 | Stoakes et al. | 324/686 |
| 5,071,527 A | * | 12/1991 | Kauffman | 205/786 |

(Continued)

FOREIGN PATENT DOCUMENTS

| EP | 0426012 A2 | | 5/1991 |
|---|---|---|---|
| EP | 1150119 A1 | | 10/2001 |
| JP | 2004008255 A | * | 1/2004 |
| JP | 2004016798 A | * | 1/2004 |

OTHER PUBLICATIONS

European Patent Office, International Search Report and Written Opinion for International Application No. PCT/US2011/048701 (counterpart to above-captioned patent application), mailed Dec. 5, 2011.

*Primary Examiner* — Joseph M Pelham
(74) *Attorney, Agent, or Firm* — Baker Botts L.L.P.

(57) ABSTRACT

A fryer measures cooking medium quality, and includes a cooking vessel configured to store a cooking medium, an electrode plate completely immersed in the cooking medium, an insulator comprising a first side and a second side, wherein the first side of the insulator is fixed to the electrode plate, and a second side of the insulator is attached to a wall of the cooking vessel, a guard ring fixed to the cooking vessel and surrounding the electrode plate and insulator. The guard ring extends further away from the wall of the cooking vessel than the electrode plate. A size of a gap between the guard ring and the electrode plate is based on a height, a width, and a thickness of the electrode plate and substantially defines a gain of the electrode. A signal conditioning circuit measures the conductivity of the cooking medium applied to the electrode.

17 Claims, 9 Drawing Sheets

(56) References Cited

U.S. PATENT DOCUMENTS

| | | | |
|---|---|---|---|
| 5,594,327 A * | 1/1997 | Sagredos et al. | 324/71.1 |
| 5,818,731 A * | 10/1998 | Mittal et al. | 702/22 |
| 5,933,016 A * | 8/1999 | Kauffman et al. | 324/698 |
| 6,274,850 B1 | 8/2001 | Mercer | |
| 6,469,521 B1 * | 10/2002 | Klun et al. | 324/658 |
| 7,504,836 B2 * | 3/2009 | Chambon et al. | 324/698 |
| 7,834,646 B2 * | 11/2010 | Chambon et al. | 324/698 |
| 8,497,691 B2 * | 7/2013 | Behle et al. | 324/698 |
| 8,519,726 B2 * | 8/2013 | Sun | 324/707 |
| 2003/0155935 A1 * | 8/2003 | Klun | 324/664 |
| 2004/0045448 A1 * | 3/2004 | Abe et al. | 99/403 |
| 2005/0212533 A1 * | 9/2005 | Itomi | 324/698 |
| 2009/0309619 A1 * | 12/2009 | Behle et al. | 324/698 |
| 2013/0036916 A1 * | 2/2013 | Burkett et al. | 99/330 |
| 2013/0278276 A1 * | 10/2013 | Behle et al. | 324/663 |

\* cited by examiner

SYSTEMS AND METHODS OF IMPLEMENTING AN ELECTRODE FOR COOKING MEDIUM QUALITY MEASUREMENT

CROSS-REFERENCE TO RELATED APPLICATIONS

This application claims the benefit of U.S. Provisional Application No. 61/375,851, filed Aug. 22, 2010, the disclosure of which is incorporated herein by reference.

BACKGROUND OF THE INVENTION

1. Field of the Invention

The present invention relates generally to systems and methods for implementing an electrode for cooking medium quality measurement, e.g., as in a fryer.

2. Description of Related Art

When preparing food in a fryer, the quality of the cooking medium, e.g., the oil, may impact the quality of the food that is cooked by the fryer. As the cooking medium is used to cook food, particles of food may contaminate the cooking medium. The flavor characteristics of each of these food products may become infused to a greater or a lesser degree in the cooking medium. This infusion may adversely affect food quality. Moreover, upon heating the cooking medium, the cooking medium may undergo chemical reactions, e.g., hydrolysis, oxidation, and polymerization. These degradations may cause products such as free fatty acids, hydroperoxides, and polymerized triglycerides. Moreover, degradation may reduce the viscosity of the cooking oils, which also may decrease performance. In many instances, such degradation of the cooking medium does not become apparent to the human eye until a late stage of degradation. Thus, there is a need to measure the quality of the cooking medium, which directly correlates to its suitability for use in cooking.

One method of measuring the quality of cooking medium uses a sense electrode immersed in the frying medium. The electrode is energized with an excitation voltage signal, and the resulting current flows from the energized electrode through the cooking medium to ground. The measured value of this current corresponds to the cooking medium quality, that is, its suitability for use for cooking. Nevertheless, known electrode systems are not suitable for use in an open fryer. First, the construction materials must withstand cooking oil temperatures up to 450 degrees Fahrenheit (230 degrees Celsius). Second, the electrode must resist mechanical damage from cleaning and operator equipment abuse. Thurs, the electrode must be sufficiently unaffected by contamination from suspended food particles, as well as from long-term varnishing by exposure to hot cooking medium.

In addition, for use in a commercial fryer, known electrodes, in addition to the above problems, are not small enough to mount in the cooking vessel below the cooking medium level, without interfering with the fry baskets or other vat mechanical features. Additionally, readouts from the electrodes must be sufficiently shielded such that they are sufficiently unaffected by the proximity of grounded metal objects in the cooking vessel, e.g., the fry baskets. Thus, the electrode must be small, but if the electrode is too small, then the electrode may not be capable of generating sufficient signal gain to generate an output signal of sufficient magnitude to resolve cooking medium quality differences with an adequate signal to noise ratio. Cooking media may have very high resistance, so the electrode current is very small, requiring a large circuit gain to create a usable signal.

Known electrodes use, for example, an interdigitated pattern of conductors deposited on a ceramic or a fiberglass substrate. These conductors have very small spacing. Such electrodes are too fragile for use in a commercial fryer. Additionally, such electrodes are too susceptible to contamination from food particles entering the small conductor spacing. Further, known electrodes, such as those described above, do not comply with food safety regulations.

SUMMARY OF THE INVENTION

Therefore, a need has arisen for systems and methods for a cooking apparatus that overcome these and other shortcomings of the related art. A technical advantage of the present invention is that an electrode unit is created that complies with food safety regulations, and is durable enough for use in a commercial fryer. Moreover, the size and geometry of the electrode determine the magnitude of the output response. As mentioned above, most cooking media have a very high resistance. The electrode current then is very small, e.g., on the order of micro-amps ($\mu A$) or nano-amps (nA). Thus, a large circuit gain is beneficial to create a usable signal. Nevertheless, artificially boosted circuit gains also amplify the system noise. This increases the need for signal filtering and processing, and also may contribute to false readings. Thus, the invention is designed to increase output from the electrode itself. The inherent output response from the electrode itself when a cooking medium of a given quality is applied to the electrode will hereinafter be referred to as "electrode gain." This invention uses particular size, geometry, design, and construction of an electrode in order to provide high electrode gain. The specific values in this invention have been carefully tested to provide high electrode gain as an unexpected result.

In an embodiment of the invention, an open fryer is configured to measure cooking medium quality within the open fryer. The open fryer comprises a cooking vessel configured to store a cooking medium, an electrode plate completely immersed in the cooking medium, an insulator comprising a first side and a second side opposite the first side, wherein the first side of the insulator is fixed to a particular side of the electrode plate, and a second side of the insulator is attached to a wall of the cooking vessel, a guard ring fixed to the cooking vessel and surrounding the electrode plate and insulator, wherein the guard ring extends further away from the wall of the cooking vessel than the insulator and the electrode plate, and wherein the guard ring is positioned to form a gap between the guard ring and the electrode plate, wherein a size of the gap is based on a height, a width, and a thickness of the electrode plate, and the gap substantially defines a gain of the electrode, and a signal conditioning circuit that measures the conductivity of the cooking medium applied to the electrode.

In another embodiment of the invention, an open fryer is configured to measure cooking medium quality within the open fryer. The open fryer comprises a cooking vessel configured to store a cooking medium, an electrode plate completely immersed in the cooking medium, an insulator comprising a first side and a second side opposite the first side, wherein the first side of the insulator is fixed to a particular side of the electrode plate, and a second side of the insulator is attached to a wall of the cooking vessel, a guard ring fixed to the cooking vessel and surrounding the electrode plate and insulator, wherein the guard ring extends further away from the wall of the cooking vessel than the insulator and the electrode plate, and wherein the guard ring is positioned to form a gap between the guard ring and the electrode plate, wherein a size of the gap is based on a height, a width, and a thickness of the electrode plate, and the gap substantially defines a gain of the electrode, and a signal conditioning circuit that measures the conductivity of the cooking medium applied to the electrode.

Other objects, features, and advantages of the present invention will be apparent to persons of ordinary skill in the art in view of the foregoing detailed description of the invention and the accompanying drawings.

BRIEF DESCRIPTION OF THE DRAWINGS

For a more complete understanding of the present invention, needs satisfied thereby, and the objects, features, and advantages thereof, reference now is made to the following description taken in connection with the accompanying drawings.

DETAILED DESCRIPTION OF EMBODIMENTS OF THE INVENTION

Preferred embodiments of the present invention, and their features and advantages, may be understood by referring to FIGS. 1-7, like numerals being used for corresponding parts in the various drawings.

Figure 1:
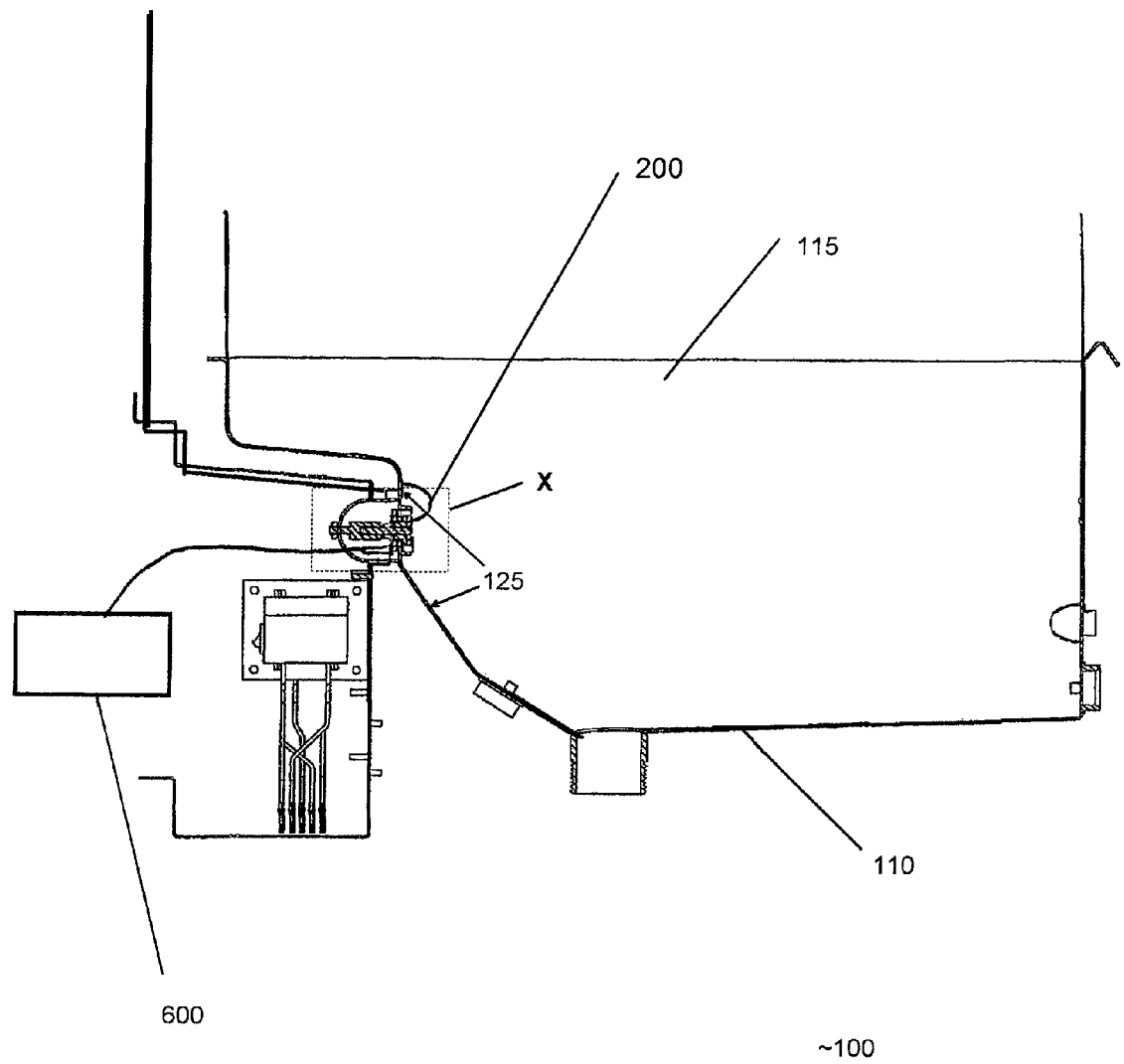
FIG. 1 is a cross-sectional view of a fryer apparatus having an electrode unit, according to an embodiment of the invention.

FIG. 1 shows a cooking medium system, such as a fryer apparatus 100, according to an embodiment of the invention. Fryer apparatus 100 may comprise at least one cooking vessel 110, e.g., a frypot, which may be configured to hold a cooking medium, e.g., an oil, a liquid shortening, a meltable-solid shortening, or the like, illustrated in FIG. 1 as cooking medium 115. Electrode unit 200, which will be described in more detail with respect to FIGS. 2-4, may measure the conductivity of cooking medium 115. Electrode unit 200 may be positioned in cooking vessel 110 and mounted to wall 125 of cooking vessel 110, such that the portions of electrode unit 200 within cooking vessel 110 may be completely submerged in cooking medium 115. Electrode unit 200 may send a signal to a signal conditioning circuit 600, which will be described in more detail with respect to FIG. 6. Signal conditioning circuit 600 measures the signal from electrode unit, and sends a signal to a controller (not shown) for further processing, e.g., alerting a user of fryer apparatus 100 if the conductivity of cooking medium 115 drops below a threshold level. The conductivity of cooking medium 115 may indicate the quality of cooking medium 115, as described in more detail previously. Fryer apparatus 100 may be configured for use in a gas or electric fryer apparatus. Although cooking vessel 110 may be suitable for an open-well fryer, fryer apparatus 100 also may be used in a pressure fryer.

Figure 2A:
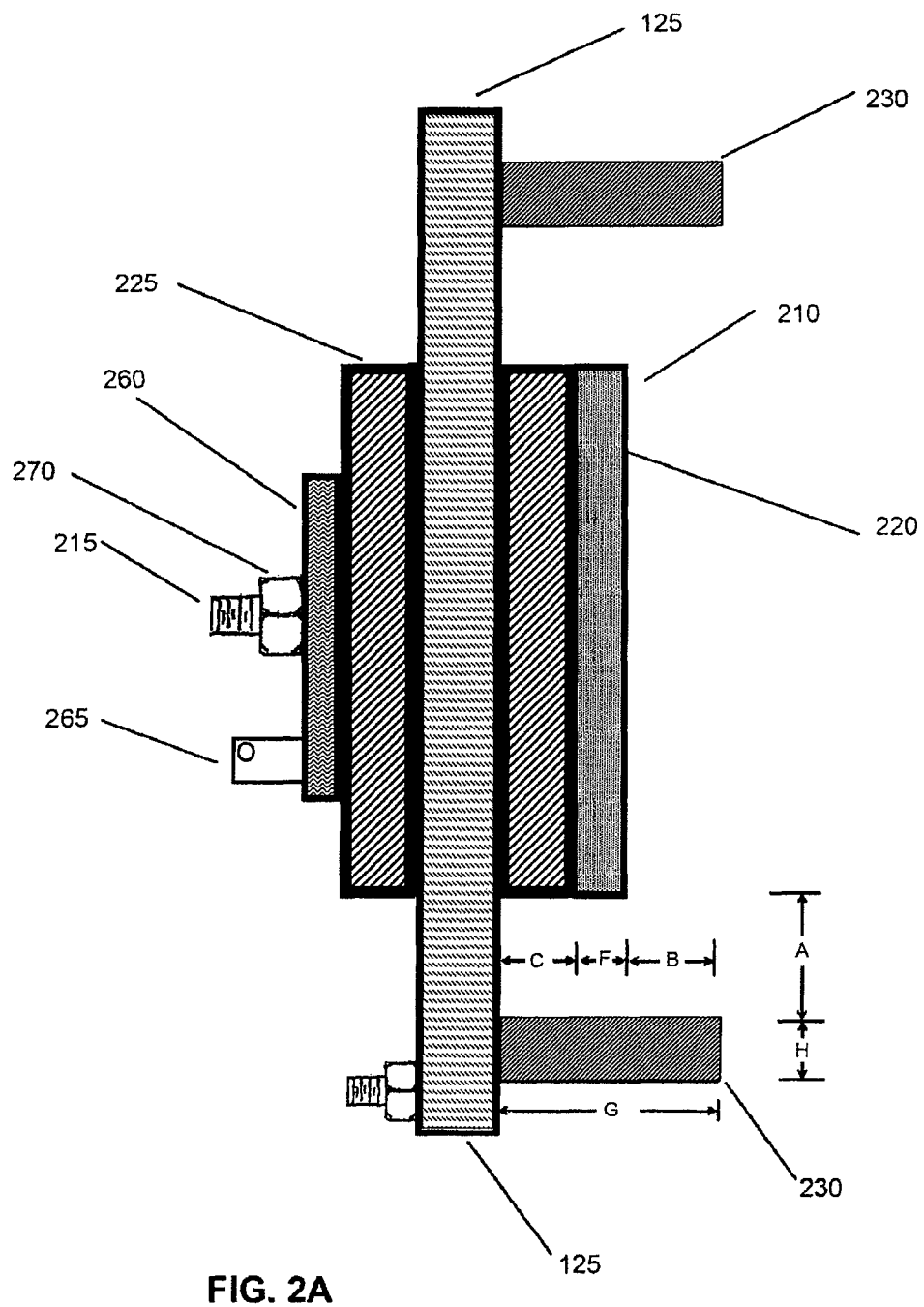
FIG. 2A is a side view of the electrode unit mounted to the wall of a cooking vessel, without the dust cover, according to an embodiment of the invention.
Figure 2B:
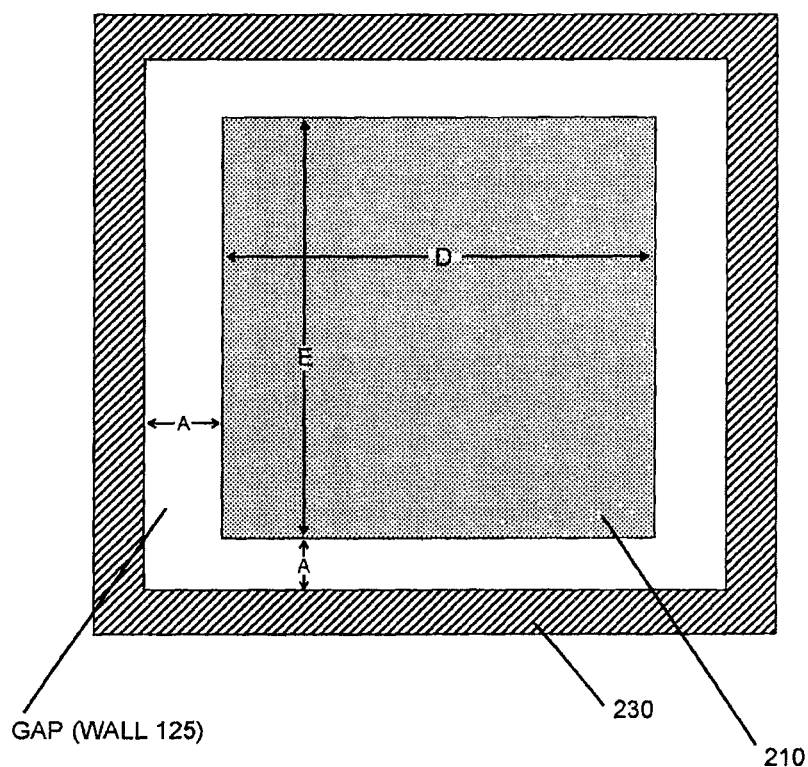
FIG. 2B is a front view of the electrode unit shown in FIG. 2A.

FIG. 2A shows a side view of electrode unit 200, as it is mounted to wall 125 of cooking vessel 110. Similarly, FIG. 2B shows a front view of electrode unit 200. FIG. 3 shows an exploded view of electrode unit 200, as it is mounted to wall 125 of cooking vessel 110. Electrode unit 200 may comprise electrode plate 210, which may comprise stainless steel. Electrode plate 210 may be polished on one side in order to create a smooth surface. In an embodiment of the invention, electrode plate 210 may be fixed to cooking vessel 110 by a flattened bolt 215, and thus, electrode plate 210 may have a hole formed at least partially through the center. In an embodiment of the invention, the hole may be formed all the way through electrode plate 210. Moreover, a portion of the hole may receive bolt 215, which will be described in more detail further herein. In an embodiment of the invention, the portion of bolt 215 that is inserted into the hole in electrode plate 210 may be unthreaded, in order to provide a smooth surface at electrode plate 210, as well as to create a tight seal to reduce or prevent cooking medium leakage.

As shown in FIG. 2B, electrode plate 210 has a width D and a height E. As shown in FIG. 2A, electrode plate 210 has a thickness F. As described above, a larger electrode produces a larger electrode gain, which corresponds to a higher quality signal generated by electrode unit 200. Nevertheless, space in cooking vessel 210 is limited by the frying baskets. Moreover, the electrode height E may be small enough such that the electrode is completely immersed in the cooking medium, even during conditions when the amount of cooking medium is low. Although other values may yield similar results, an embodiment of the invention uses a width D of electrode plate 210 of 2.000 inches (5.080 centimeters), a height E of 0.750 inches (1.905 centimeters), and a thickness of 0.105 inches (0.2667 centimeters). These values were calculated to work particularly with the other values described in this application, particularly of the dimensions of the gap described herein. Other values of these dimensions may be appropriate, but these particular values yield the unexpected result of a relatively high electrode gain with a relatively low electrode size.

As described above, one side of electrode plate 210 may face the interior of cooking vessel 110. The opposite side of electrode plate 210 may be pressed against plate insulator 220. Plate insulator 220 may be a molded body comprising polytetraflouroethylene ("PTFE"). Plate insulator 220 may comprise raised corners 225 which may assist in locating the insulator during assembly, and which may reduce or prevent rotation of plate insulator 220 during use. Plate insulator 220 also may include a hole formed therethrough, such that plate insulator 220 also may be threaded through bolt 215. In an embodiment of the invention, plate insulator 220 may comprise two separated silicone washers (not shown) in order to provide a tighter fit, to reduce or prevent cooking medium leakage through the hole in plate insulator 220. As shown in FIG. 2A, when installed, plate insulator 220 sits between wall 125 of cooking vessel 110, and electrode plate 210, and is aligned with electrode plate 210 in the width and height directions. Plate insulator 220 has a thickness C, which also may affect the electrode gain of electrode unit 200. Although a thinner plate insulator 220 may increase the electrode gain, the thinner plate insulator 220 also may increase the risk that suspended food particles may bridge electrode plate 210 and wall 125. In an embodiment of the invention, plate insulator 220 has a thickness C of 0.0930 inches (0.2362 centimeters).

In an embodiment of the invention, plate insulator 220 also has the same width and height as electrode plate 210, e.g., width D and height E. If plate insulator 220 has a larger width or height than electrode plate 210, then the electrode gain may decrease rapidly. Moreover, if plate insulator 220 has a smaller width or height than electrode plate 210, then the electrode gain may increase, but the risk of contamination increases, because suspended food particles may become trapped between wall 125 and electrode plate 210.

Guard ring 230 may comprise a steel ring that surrounds electrode plate 210 and plate insulator 220. Guard ring 230 may comprise a steel tubing, and may be formed by bending or machining a rectangular steel tubing into a ring. In another embodiment of the invention, guard ring 230 may be formed by welding and bending a strip of sheet stock. Guard ring 230 may be fastened to wall 125 through any conventional means. In an embodiment of the invention, guard ring 220 is welded to wall 125. In another embodiment of the invention, guard ring 220 is integrally formed with wall 125. Guard ring 230 may be positioned to surround electrode plate 210, leaving a gap of distance A between each wall of electrode plate 210 and corresponding wall of guard ring 230, as shown in FIGS. 2A and 2B. Distance A also may affect the electrode gain of electrode unit 200. A smaller gap may increase the electrode gain, but a smaller gap also may expose the electrode unit to collecting suspended food particles in the gap, which may decrease the accuracy of electrode unit 200. In an embodiment of the invention, distance A of the gap formed by guard ring 230 may be 0.167 inches (0.424 centimeters).

As shown in FIG. 2A, guard ring 230 has a thickness H. The thickness H of guard ring 230 may affect the electrode gain of electrode unit 200, but by a less significant margin than the dimensions listed above. Moreover, the primary purpose of guard ring 230 may be to protect the electrode plate 210 and insulator 220. Thus, the thickness H may be selected to provide sufficient mechanical strength to protect electrode plate 210 and insulator 220 from damage. In an embodiment of the invention, thickness H of guard ring 230 may be within a range of 0.075 inches to 0.083 inches (0.191 centimeters to 0.211 centimeters). Similarly, guard ring 230 extends outward from wall 125 for a distance G, as shown in FIG. 2A. Guard ring 230 may be designed to have a distance G based on the thickness of electrode plate 210 and insulator 220, and also based on the desired electrode offset for increasing electrode gain. In an embodiment of the invention, the distance G that guard ring 230 extends from wall 125 may be 0.250 inches (0.6350 centimeters). Referring again to FIG. 2A, insulator 220 and electrode plate 210 are offset below the edge of guard ring 230 to provide additional protection from damage and abuse. In FIG. 2A, the distance B may be the difference between distance G and the sum of thicknesses C and F. Distance B may be 0.057 inches (0.145 centimeters).

Guard ring 230, insulator 220, and electrode plate 210 may be positioned on an interior side of wall 125 of cooking vessel 110, as shown in FIGS. 2A and 3. In an embodiment of the invention, insulator 220, electrode plate 210, and wall 125 have a hole in their center, such that bolt 215 may pass between them, and mount electrode plate 210 and insulator 220 to wall 125. Nevertheless, as shown in FIG. 2A, back insulator 225 may be positioned next to wall 125 on an outside of wall 125, opposite the side which contacts insulator 220. Back insulator 225 may comprise PTFE, and may help reduce or prevent cooking medium from leaking through the hole in wall 125. In an embodiment of the invention, back insulator 225 also may have a hole formed therethrough, through which bolt 215 may pass.

Figure 3A:
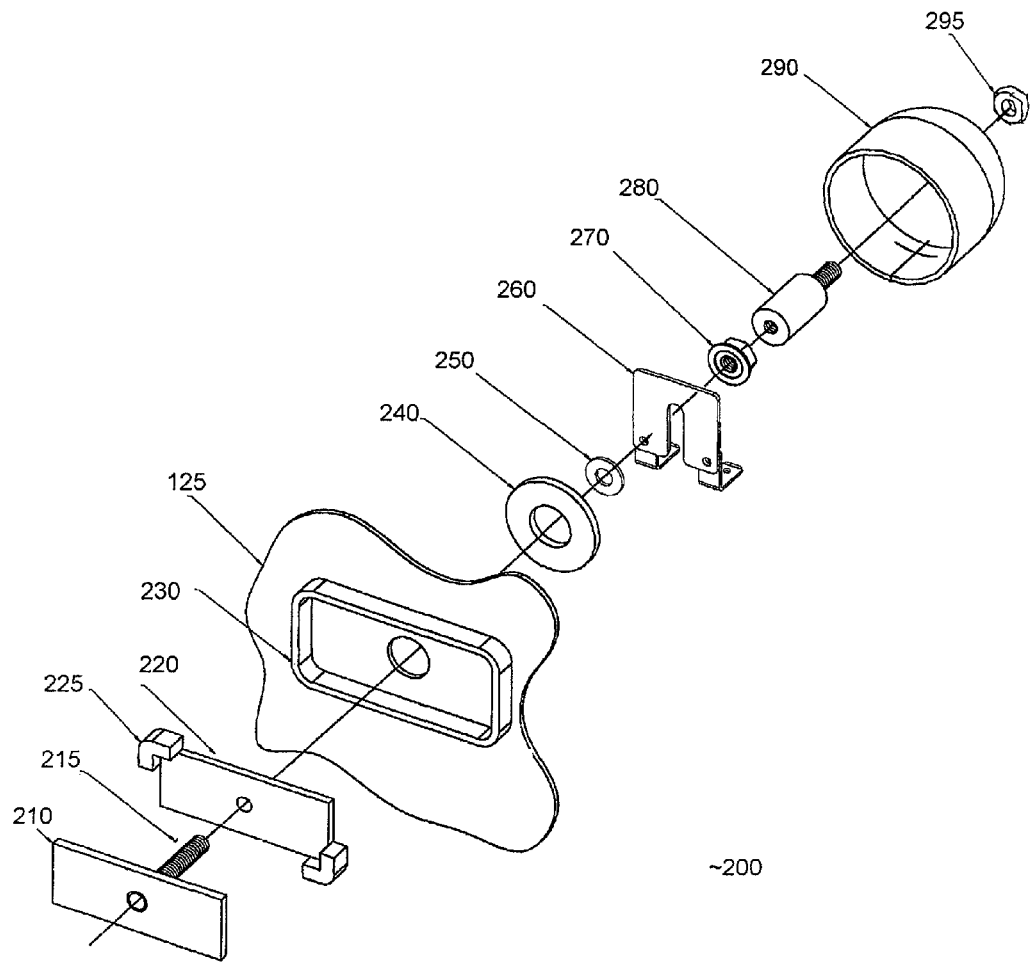
FIG. 3A is an exploded view of the electrode unit, according to an embodiment of the invention.

As shown in FIG. 3A, seal compression washer 240 also may be positioned behind wall 125. Seal washer 240 may contact back insulator 225 (not shown in FIG. 3A) and compress back insulator 225 against the outside surface of wall 125, to create a tighter seal to reduce or prevent cooking medium from leaking out of the hole in wall 125. Seal washer 240 may comprise stainless steel or another suitable material. Also, as shown in FIG. 3A, seal compression washer 250 may further compress seal washer 240, thereby tightening the seal to reduce or prevent cooking medium from leaking out of the hole in wall 125.

As shown in FIGS. 2A and 3A, an electrode contact 260 may be positioned on the opposite side of wall 125 from electrode 220. Electrode contact 260 may comprise a base plate and two terminals 265 positioned on each side of electrode contact 260, as shown in FIGS. 2A and 3. Although electrode contact 260 may comprise two terminals 265, only one terminal 265 is connected to a signal conditioning circuit, such as signal conditioning circuit 600 or 700, described in more detail herein. The other terminal 265 may balance electrode contact 260, but is not necessarily connected to the signal conditioning circuit. Either of the two terminals 265 may be used to connect electrode contact 260 to the signal conditioning circuit. Electrode contact 260 may be electrically connected to electrode plate 210.

As shown in FIGS. 2A and 3A, a nut 270 may be placed on an outside end of bolt 215, to secure electrode contact 260, seal compression washer 250, and seal washer 240 on an outside of wall 125, and plate insulator 220 and electrode plate 210 on an inside of wall 125. Nut 270 may comprise stainless steel or other suitable material, and ensures that there is a conduction path between electrode contact 260 and electrode plate 210. Moreover, as shown in FIG. 2A, electrode unit 200 also comprises a ground stud 205, which grounds electrode plate 210. A ground connection (not shown) grounds electrode plate 210 to ground stud 205, which is secured, e.g., welded, to cooking vessel 110.

Figure 3B:
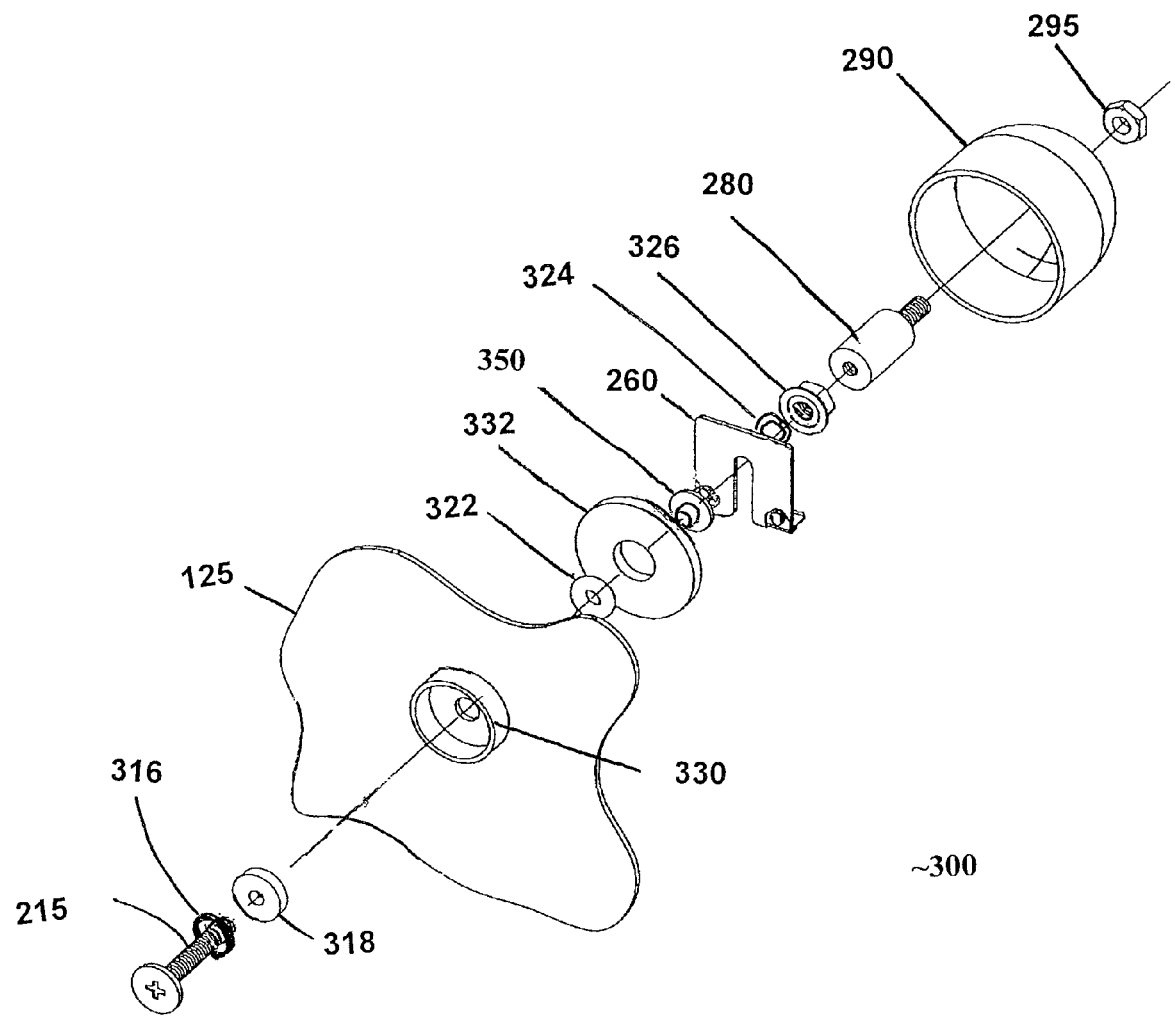
FIG. 3B is an exploded view of the electrode unit, according to another embodiment of the invention.

As noted above, FIG. 3B is an exploded view of an electrode unit 300, according to another embodiment of the invention. In FIGS. 3A and 3B like numbers are used to described similar parts. As shown in FIG. 3B, a first seal washer 322 and a second seal washer 332 also may be positioned behind wall 125. First seal washer 322 may contact one surface of an insulating washer 318 and compress insulating washer 318 against the outside surface of wall 125, to create a tighter seal to reduce or prevent cooking medium from leaking out of the hole in wall 125. First seal washer 322 may comprise silicon or another suitable material, and second seal washer 332 may comprise PTFE or another suitable material. In addition, as shown in FIG. 3B, a seal compression sleeve 350 may further compress first seal washer 322 and second seal washer 332, thereby tightening the seal to reduce or prevent cooking medium from leaking out of the hole in wall 125.

As shown in FIG. 3B, electrode contact 260 may be positioned on the opposite side of wall 125 from an electrode (not shown). Electrode contact 260 may comprise a base plate and two terminals positioned on each side of electrode contact 260, as shown in FIG. 3B. Although electrode contact 260 may comprise two terminals, only one terminal is connected to a signal conditioning circuit, such as signal conditioning circuit 600 or 700, described in more detail herein. The other terminal may balance electrode contact 260, but is not necessarily connected to the signal conditioning circuit. Either of the two terminals may be used to connect electrode contact 260 to the signal conditioning circuit. Electrode contact 260 may be electrically connected to an electrode plate (not shown).

As shown in FIG. 3B, a nut 326 may be placed on an outside end of bolt 215, to secure electrode contact 260, seal compression sleeve 350, and first seal washer 322 and second seal washer 332 on an outside of wall 125, and the plate insulator and the electrode plate on an inside of wall 125. Nut 326 may comprise stainless steel or other suitable material, and ensures that there is a conduction path between electrode contact 260 and the electrode plate. Moreover, an electrode unit (not shown) also comprises a ground stud, which grounds the electrode plate. A ground connection (not shown) grounds the electrode plate to the ground stud, which is secured, e.g., welded, to cooking vessel 110.

Figure 4:
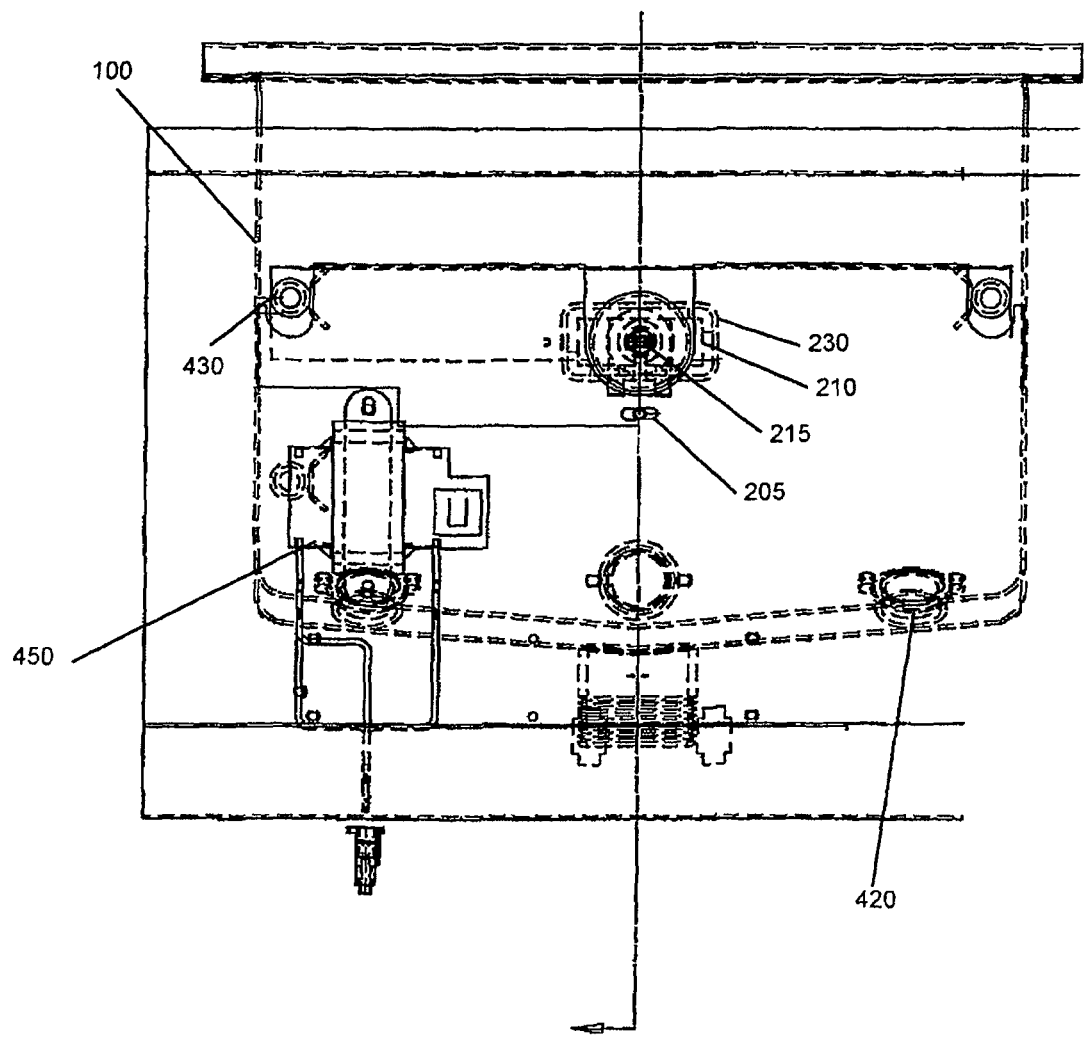
FIG. 4 is a front view of the cooking vessel, with the front wall of the cooking vessel cut out so that the electrode unit is visible, according to an embodiment of the invention.

FIG. 4 shows fryer apparatus 100 from a front view. The front walls of fryer apparatus 100 have been cut away to illustrate electrode 210, guard ring 230, bolt 215, and ground stud 205. These cut-away front walls are represented by dotted lines in FIG. 4. FIG. 4 also shows the positional relationship between electrode unit 200 and other parts of the fryer apparatus 100, e.g., cooking medium outlet 420, cooking medium inlet 430, and sensor mechanism 450.

Figure 5:
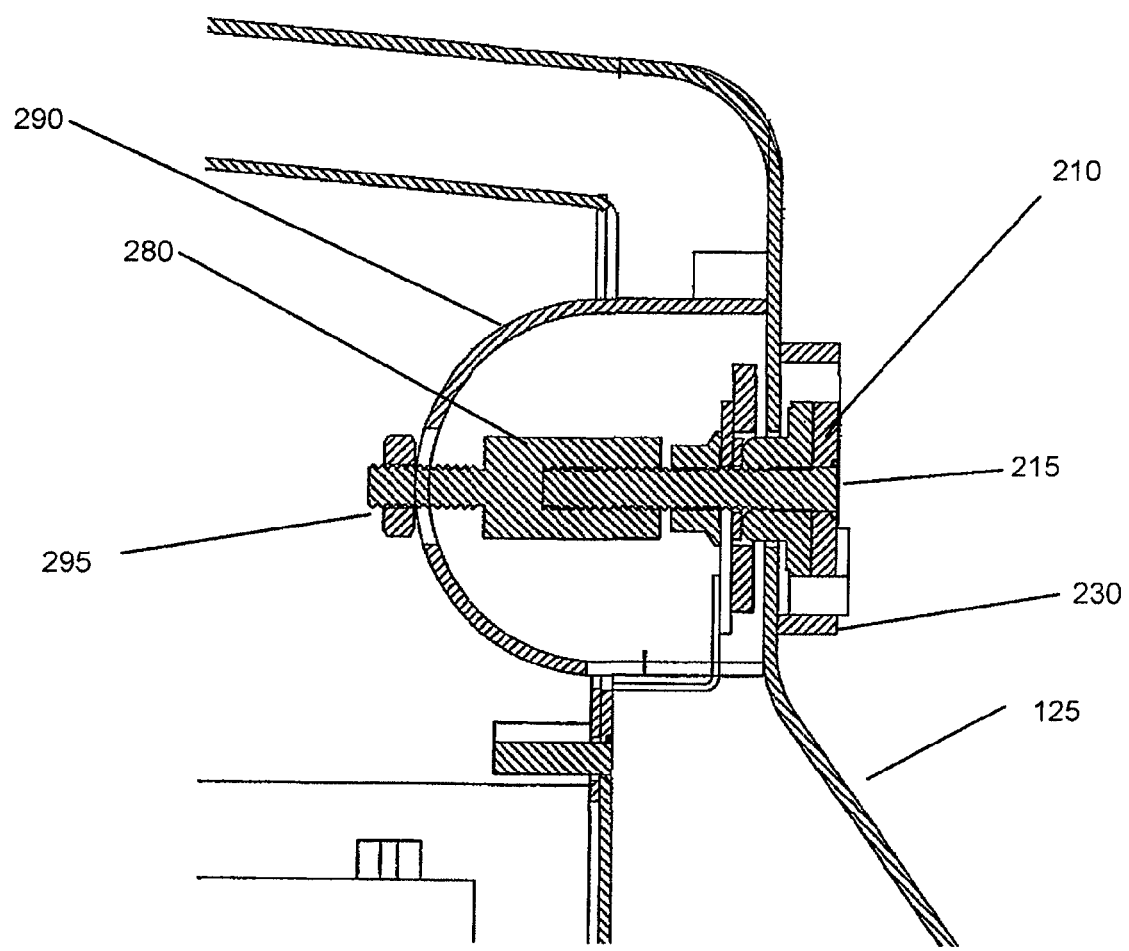
FIG. 5 is a cross-sectional, enlarged view of the dotted-line box shown in FIG. 1, showing a cross-section of the electrode unit, and also showing the dust cover, according to an embodiment of the invention.

FIG. 5 shows an enlarged view of box X of FIG. 1. Particularly, FIG. 5 shows electrode unit 200, surrounded by dust cover 290. As shown in FIGS. 3A, 3B, and 5, dust cover 290, dust cover spacer 280, and dust cover nut 295, may be included in fryer apparatus 100, and will be discussed in more detail herein. In another embodiment of the invention, dust cover 290, dust cover spacer 280, and dust cover nut 295 may be omitted.

As shown in FIGS. 3A, 3B, and 5, dust cover 290 may be held in place by dust cover spacer 280, which may be screwed onto the end of bolt 215. Although FIG. 5 does not show nut 270, in an embodiment of the invention, nut 270 remains on bolt 215 to maintain a tight seal of the hole through wall 215, and to ensure electrical conductivity between electrode plate 210 and electrode contact 260. Dust cover spacer 280 may comprise a wide portion at one end, which may surround bolt 215, and a narrow portion at the other end, which may be threaded. Dust cover spacer 280 may provide electrically insulated spacing to the dust cover 290 away from electrode contact 260, such that electrode gain may not be affected by dust cover 290. In an embodiment of the invention, dust cover spacer 280 may comprise a durable material with a very low electrical conductivity, e.g., PTFE. As shown in FIG. 5, a central portion of dust cover 290 may be threaded through the other end of dust cover spacer 280. Dust cover nut 295 then may be threaded onto the other end of dust cover spacer 280, such that dust cover 290 is secured. Dust cover 290 may comprise a silicone rubber.

In an embodiment of the invention, dust cover 290 may contain a slit (not shown), which may be configured to allow entry of a wire to reach electrode contact terminal 265, which is not pictured in this illustration. Electrode contact 260 and electrode contact terminal 265 may be modified in order to accommodate dust cover 290 and slit 265. In an embodiment of the invention, dust cover 290 prevents accumulation of foreign material, e.g., breading dust and cooking medium film, around the electrode contact area.

Figure 6:
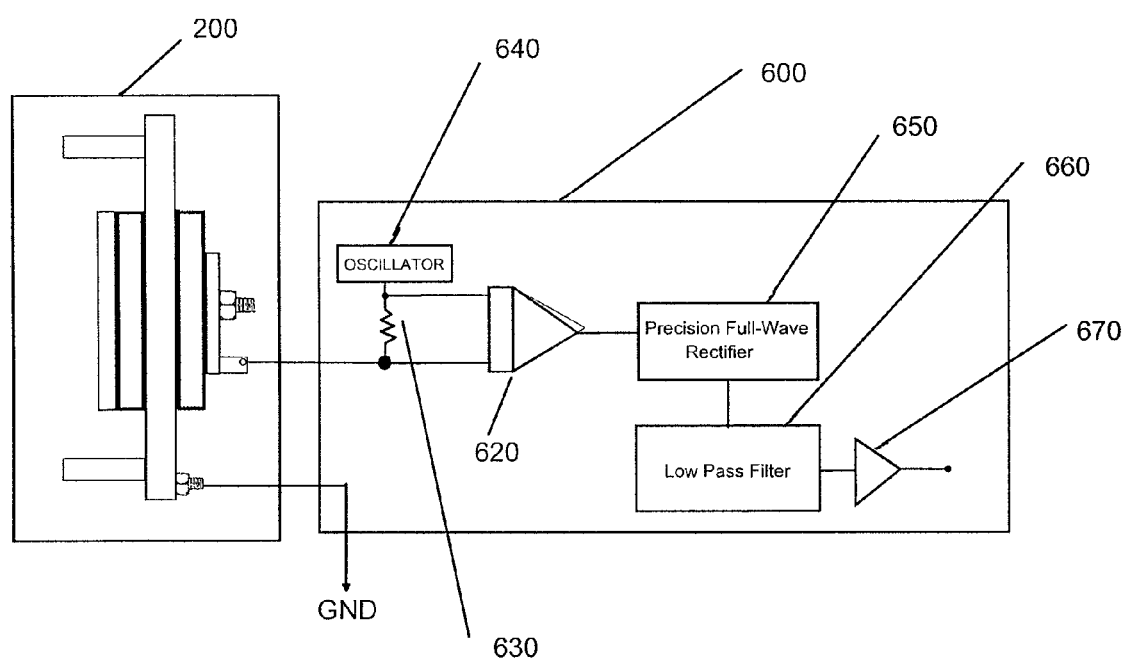
FIG. 6 shows the signal conditioning circuit, according to an embodiment of the invention.

FIG. 6 shows a high-level diagram of signal conditioning circuit 600. The complete details of this circuit are omitted, but the enclosed description is sufficient for one of ordinary skill in the art to construct this circuit. The signal conditioning circuit 600 may be powered by a ±5V DC power supply. Within the signal conditioning circuit, oscillator 640 may create the electrode excitation signal, which in an embodiment of the invention, may be a ±2.5V square wave, with a frequency of approximately 10 Hz. The duty cycle for this square wave may be approximately 50%. The excitation signal may be applied to the electrode from oscillator 640 through resistor 630. Thus, the current that flows through the cooking medium in the cooking vessel 110 may develop a voltage potential across resistor 630 having a value R. The voltage across resistor 630 may be amplified by instrumentation amplifier 620. Then, the voltage from instrumentation amplifier 620 may be rectified by precision full-wave rectifier 650. The rectifier output then may be applied to low-pass filter 660, and finally may pass through gain stage amplifier 670. The output of gain stage amplifier 670 may be a voltage proportional to the DC current flow through the cooking medium. In an embodiment of the invention, the value R may be 499 kilo-ohms (KΩ). Nevertheless, this resistor value is based on the various dimensions described above for electrode unit 200, and other embodiments may have other values.

Figure 7:
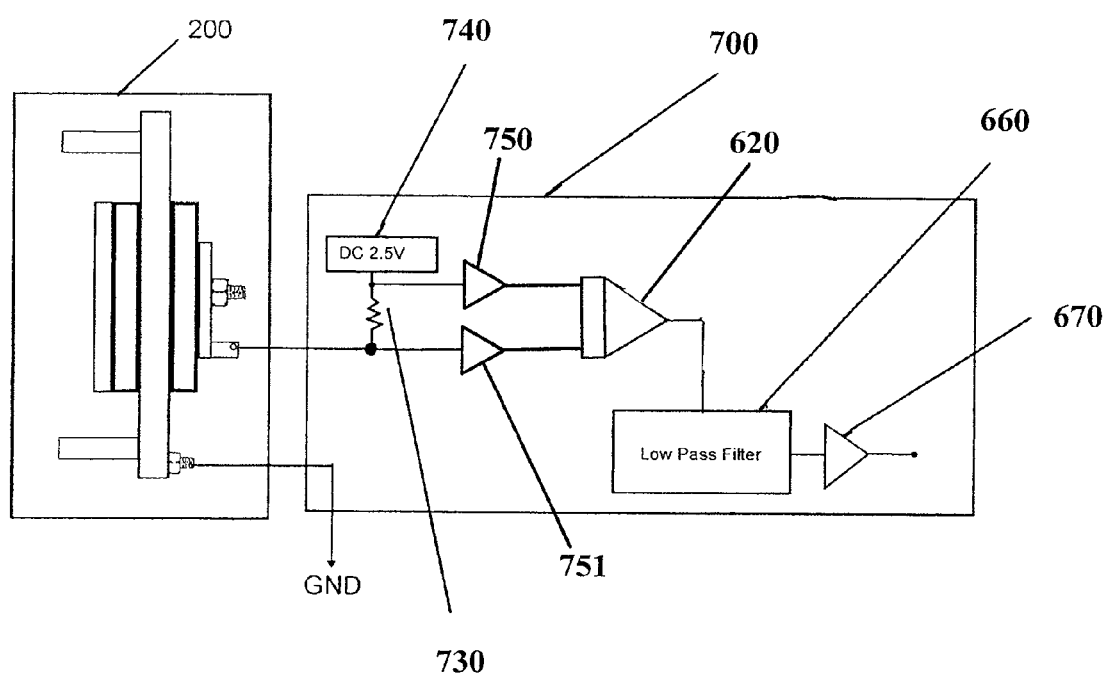
FIG. 7 shows the signal conditioning circuit, according to another embodiment of the invention.

FIG. 7 shows a high-level diagram of signal conditioning circuit 700. In FIGS. 6 and 7 like numbers are used to described similar parts. The complete details of this circuit are omitted, but the enclosed description is sufficient for one of ordinary skill in the art to construct this circuit. The signal conditioning circuit 700 may be powered by a ±5V DC power supply. Within the signal conditioning circuit, a DC voltage reference 740 may create the electrode excitation signal, which in an embodiment of the invention, may be 3V DC. The excitation may be applied to the electrode from DC voltage reference 740 through a resistor 730. Thus, the current that flows through the cooking medium in cooking vessel 110 may develop a voltage potential across resistor 730 having a value R. Voltage across resistor 730 may be buffered by voltage buffers 750 and 751. The buffered voltage may be amplified by instrumentation amplifier 620. The instrumentation amplifier output may then be applied to low-pass filter 660, and finally pass through gain stage amplifier 670. The output of gain stage amplifier 670 may be a voltage proportional to the DC current flow through the cooking medium. In an embodiment of the invention, the value R may be about 499 kilo-ohms (KΩ). Nevertheless, this resistor value is based on the various dimensions described above for electrode unit 200, and other embodiments may have different and appropriate values.

While the invention has been described in connection with preferred embodiments, it will be understood by those of ordinary skill in the art that other variations and modifications of the preferred embodiments described above may be made without departing from the scope of the invention. Other embodiments will be apparent to those of ordinary skill in the art from a consideration of the specification or practice of the invention disclosed herein. The specification and the described examples are considered as exemplary only, with the true scope and spirit of the invention indicated by the following claims.

What is claimed is:

1. An electrode unit for use in a fryer system, the electrode unit comprising:
   an electrode plate comprising a first side and a second side opposite the first side, the electrode plate configured to be completely immersed in cooking medium, the electrode plate having a height, a width, and a thickness;
   an insulator formed on the first side of the electrode plate and covering a surface of the electrode defined by the height and the width;
   a guard ring surrounding the electrode plate, wherein the guard ring is positioned to form a gap between the guard ring and the electrode plate in the height and the width directions, wherein a size of the gap is defined at least by the height, width, and thickness of the electrode plate, and the gap substantially defines a gain of the electrode; and the second side of the electrode plate is a smooth polished surface.

2. The electrode unit of claim 1, further comprising: a signal conditioning circuit configured to receive a signal from the electrode plate, and to measure the conductivity of the cooking medium in which the electrode is completely immersed based on the received signal.

3. The electrode unit of claim 1, wherein the height of the electrode is 1.905 cm, and the width of the electrode is 5.08 cm.

4. The electrode unit of claim 3, wherein the gap is 0.424 cm from each side of the electrode plate to its corresponding side of the guard ring.

5. The electrode unit of claim 4, wherein the insulator thickness is 0.2362 cm and the electrode plate thickness is 0.2667 cm.

6. The electrode unit of claim 5, wherein the guard ring extends 0.145 cm beyond the electrode plate.

7. The electrode unit of claim 6, wherein the guard ring has a thickness of 0.2667 cm.

8. The electrode unit of claim 1, wherein the guard ring comprises an electrically conductive stainless steel.

9. The electrode unit of claim 8, wherein the insulator comprises PTFE.

10. A fryer configured to measure cooking medium quality within the fryer, the fryer comprising:
a cooking vessel configured to store a cooking medium;
an electrode plate completely immersed in the cooking medium;
an insulator comprising a first side and a second side opposite the first side, wherein the first side of the insulator is fixed to a particular side of the electrode plate, and a second side of the insulator is attached to a wall of the cooking vessel;
a guard ring fixed to the cooking vessel and surrounding the electrode plate and insulator, wherein the guard ring extends further away from the wall of the cooking vessel than the insulator and the electrode plate, and wherein the guard ring is positioned to form a gap between the guard ring and the electrode plate, wherein a size of the gap is defined at least by a height, a width, and a thickness of the electrode plate, and the gap substantially defines a gain of the electrode; and
a signal conditioning circuit that measures the conductivity of the cooking medium applied to the electrode.

11. The fryer of claim 10, wherein the electrode plate comprises a further side opposite the particular side, and the further side of the electrode plate is a polished smooth surface.

12. The fryer of claim 10, further comprising:
a seal washer positioned on an opposite side of the wall of the cooking vessel from the insulator and configured to prevent cooking medium from escaping the cooking vessel at the electrode plate;
a seal compression washer positioned on the opposite side of the wall of the cooking vessel and configured to compress the seal washer against the opposite side of the wall of the cooking vessel; and
a back insulator positioned on the opposite side of the wall of the cooking vessel, wherein the back insulator covers the seal compression washer and is aligned with the insulator.

13. The fryer of claim 12, further comprising a bolt threaded through the electrode plate, the insulator, the wall of the cooking vessel, the seal washer, the seal compression washer, and the back insulator.

14. The fryer of claim 13, further comprising:
a dust cover spacer comprising a first end and a second end opposite the first end, wherein the first end is threaded through an end of the bolt outside the cooking vessel, and the second end of the dust cover spacer is threaded;
a dust cover positioned on the opposite side of the wall that covers the seal washer, seal compression washer, and back insulator, wherein a center of the dust cover is threaded through the second end of the dust cover spacer; and
a dust cover nut threaded through the second end of the dust cover spacer, and that fixes the dust cover to the dust cover spacer.

15. The fryer of claim 10, wherein the guard ring is integrally formed with the cooking vessel.

16. The fryer of claim 10, wherein the guard ring comprises a steel rectangular tubing.

17. The fryer of claim 10, wherein the guard ring comprises a fabricated steel stock.

* * * * *